United States Patent
Zhou et al.

(10) Patent No.: US 10,117,659 B2
(45) Date of Patent: *Nov. 6, 2018

(54) SUBINTIMAL RE-ENTRY CATHETER WITH ACTUATABLE ORIENTATION MECHANISM

(71) Applicant: BOSTON SCIENTIFIC SCIMED, INC., Maple Grove, MN (US)

(72) Inventors: Pu Zhou, Trabuco Canyon, CA (US); Huisun Wang, Maple Grove, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 102 days.

This patent is subject to a terminal disclaimer.

(21) Appl. No.: 15/250,075

(22) Filed: Aug. 29, 2016

(65) Prior Publication Data

US 2016/0361076 A1    Dec. 15, 2016

Related U.S. Application Data

(63) Continuation of application No. 14/154,774, filed on Jan. 14, 2014, now Pat. No. 9,451,984.

(Continued)

(51) Int. Cl.
*A61M 29/00* (2006.01)
*A61B 17/22* (2006.01)
(Continued)

(52) U.S. Cl.
CPC .......... *A61B 17/22* (2013.01); *A61B 17/3207* (2013.01); *A61B 17/3478* (2013.01);
(Continued)

(58) Field of Classification Search
CPC . A61B 17/22; A61B 17/3478; A61B 17/3207; A61M 25/0169; A61M 25/0074; A61M 25/0071; A61M 25/0108
See application file for complete search history.

(56) References Cited

U.S. PATENT DOCUMENTS

| 6,506,178 B1 | 1/2003 | Schubart et al. |
| 6,726,677 B1 | 4/2004 | Flaherty et al. |

(Continued)

FOREIGN PATENT DOCUMENTS

WO     2013003194 A1    1/2013

*Primary Examiner* — Richard Louis
(74) *Attorney, Agent, or Firm* — Seager, Tufte & Wickhem LLP (57) ABSTRACT

A recanalization catheter for facilitating re-entry into a lumen of a blood vessel from a subintimal space. The recanalization catheter includes first and second mechanically actuatable wings positioned at a distal region of the elongate shaft of the catheter that are actuatable between a retracted position and an expanded position. In the retracted position the mechanically actuatable wings are positioned in first and second elongate channels defined in the elongate shaft, and in the expanded position the mechanically actuatable wings extend outward from the first and second elongate channels. The actuatable wings extend in an arcuate path away from the elongate shaft in the expanded position to be positionable in a circumferential orientation within a subintimal space formed in a vessel wall to automatically orient a lateral port of the elongate shaft toward the true lumen.

18 Claims, 9 Drawing Sheets

Related U.S. Application Data

(60) Provisional application No. 61/752,498, filed on Jan. 15, 2013.

(51) Int. Cl.
*A61B 17/3207* (2006.01)
*A61B 17/34* (2006.01)
*A61M 25/00* (2006.01)
*A61M 25/01* (2006.01)
*A61B 90/00* (2016.01)

(52) U.S. Cl.
CPC .... *A61M 25/0071* (2013.01); *A61M 25/0074* (2013.01); *A61M 25/0108* (2013.01); *A61M 25/0169* (2013.01); *A61B 2017/22044* (2013.01); *A61B 2017/22095* (2013.01); *A61B 2090/3966* (2016.02)

(56) References Cited

U.S. PATENT DOCUMENTS

| | | |
|---|---|---|
| 2003/0109809 A1 | 6/2003 | Jen et al. |
| 2004/0210240 A1* | 10/2004 | Saint ............... A61B 17/00234 606/139 |
| 2006/0167437 A1* | 7/2006 | Valencia ............... A61M 25/00 604/523 |
| 2009/0209910 A1 | 8/2009 | Kugler et al. |
| 2009/0230167 A1 | 9/2009 | Xiao et al. |

* cited by examiner

SUBINTIMAL RE-ENTRY CATHETER WITH ACTUATABLE ORIENTATION MECHANISM

CROSS-REFERENCES TO RELATED APPLICATIONS

This application is a continuation application of U.S. application Ser. No. 14/154,774, filed Jan. 14, 2014 which claims the benefit of priority under 35 U.S.C. § 119(e) of U.S. Provisional Patent Application Ser. No. 61/752,498, filed on Jan. 15, 2013, which are herein incorporated by reference in their entirety.

TECHNICAL FIELD

The disclosure is directed to devices and methods for recanalization of an occluded blood vessel. More particularly, the disclosure is directed to devices and methods for re-entry into the true lumen from the extraluminal or subintimal space of a blood vessel.

BACKGROUND

Chronic total occlusion (CTO) is an arterial vessel blockage that obstructs blood flow through the vessel, and can occur in both coronary and peripheral arteries. In some instances, it may be difficult or impossible to pass through the CTO with a medical device in an antegrade direction to recanalize the vessel. Accordingly, techniques have been developed for creating a subintimal pathway (i.e., a pathway between the intimal and adventitial tissue layers of the vessel) around the occlusion and then re-entering the true lumen of the vessel distal of the occlusion in an attempt to recanalize the vessel. In some instances re-entering the true lumen from the subintimal space and/or recanalization can be difficult. Accordingly, it is desirable to provide alternative recanalization devices and/or methods of recanalizing a blood vessel in which a CTO is present.

SUMMARY

The disclosure is directed to several alternative designs, materials and methods of manufacturing medical device structures and assemblies, and uses thereof.

Accordingly, one illustrative embodiment is a recanalization catheter for facilitating re-entry into a lumen of a blood vessel from a subintimal space. The recanalization catheter includes an elongate shaft extending distally from a hub assembly. The elongate shaft includes a guidewire lumen. The recanalization catheter also includes first and second mechanically actuatable wings positioned at a distal region of the elongate shaft. The first and second mechanically actuatable wings are actuatable between a retracted position and an expanded position with an actuation mechanism extending through the elongate shaft to the hub assembly. The distal region of the elongate shaft includes first and second elongate channels opening out to an exterior of the elongate shaft. In the retracted position the first and second mechanically actuatable wings are positioned in the first and second elongate channels, respectively, and in the expanded position the first and second mechanically actuatable wings extend outward from the first and second elongate channels, respectively.

Another illustrative embodiment is a recanalization catheter for facilitating re-entry into a lumen of a blood vessel from a subintimal space. The recanalization catheter includes an elongate shaft extending distally from a hub assembly. The elongate shaft includes a guidewire lumen, first and second elongate channels formed in the distal region of the elongate shaft and opening out to an exterior of the elongate shaft, and first and second auxiliary lumens extending through the elongate shaft to the first and second elongate channels, respectively. The elongate shaft also includes a distal opening and a lateral opening in a distal region of the elongate shaft proximal of the distal opening, each communicating with the guidewire lumen. The recanalization catheter further includes a first mechanically actuatable wing and a second mechanically actuatable wing. The first mechanically actuatable wing is positioned at the distal region of the elongate shaft and is actuatable between a retracted position and an expanded position. The second mechanically actuatable wing is also positioned at the distal region of the elongate shaft and is actuatable between a retracted position and an expanded position. In the retracted position, the first and second mechanically actuatable wings are positioned in the first and second elongate channels, respectively. In the expanded position the first and second mechanically actuatable wings extend outward from the first and second elongate channels, respectively. The first and second actuatable wings curve towards the lateral port in the expanded position such that the lateral port is oriented toward the lumen of the blood vessel when the first and second actuatable wings are in the expanded position in the subintimal space formed in the blood vessel.

Yet another illustrative embodiment is a method of recanalizing a blood vessel having an occlusion therein. The method includes advancing a distal region of a catheter shaft including first and second mechanically actuatable wings positioned in a retracted position into a subintimal space between a first tissue layer and a second tissue layer of a wall of a blood vessel such that the first and second mechanically actuatable wings are positioned in the subintimal space distal to the occlusion. In the retracted position, the first and second actuatable wings are positioned in first and second elongate channels formed on opposite sides of the distal region of the catheter shaft. The first and second mechanically actuatable wings may then be actuated outward from the first and second elongate channels to an expanded configuration to orient a lateral port in the distal region of the catheter shaft toward a lumen of the blood vessel distal of the occlusion. A penetration member may then be advanced from the lateral port of the catheter shaft to penetrate through the first tissue layer into the lumen of the blood vessel.

The above summary of some example embodiments is not intended to describe each disclosed embodiment or every implementation of the aspects of the disclosure.

BRIEF DESCRIPTION OF THE DRAWINGS

The aspects of the disclosure may be more completely understood in consideration of the following detailed description of various embodiments in connection with the accompanying drawings, in which.

While the aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

Figure 1:
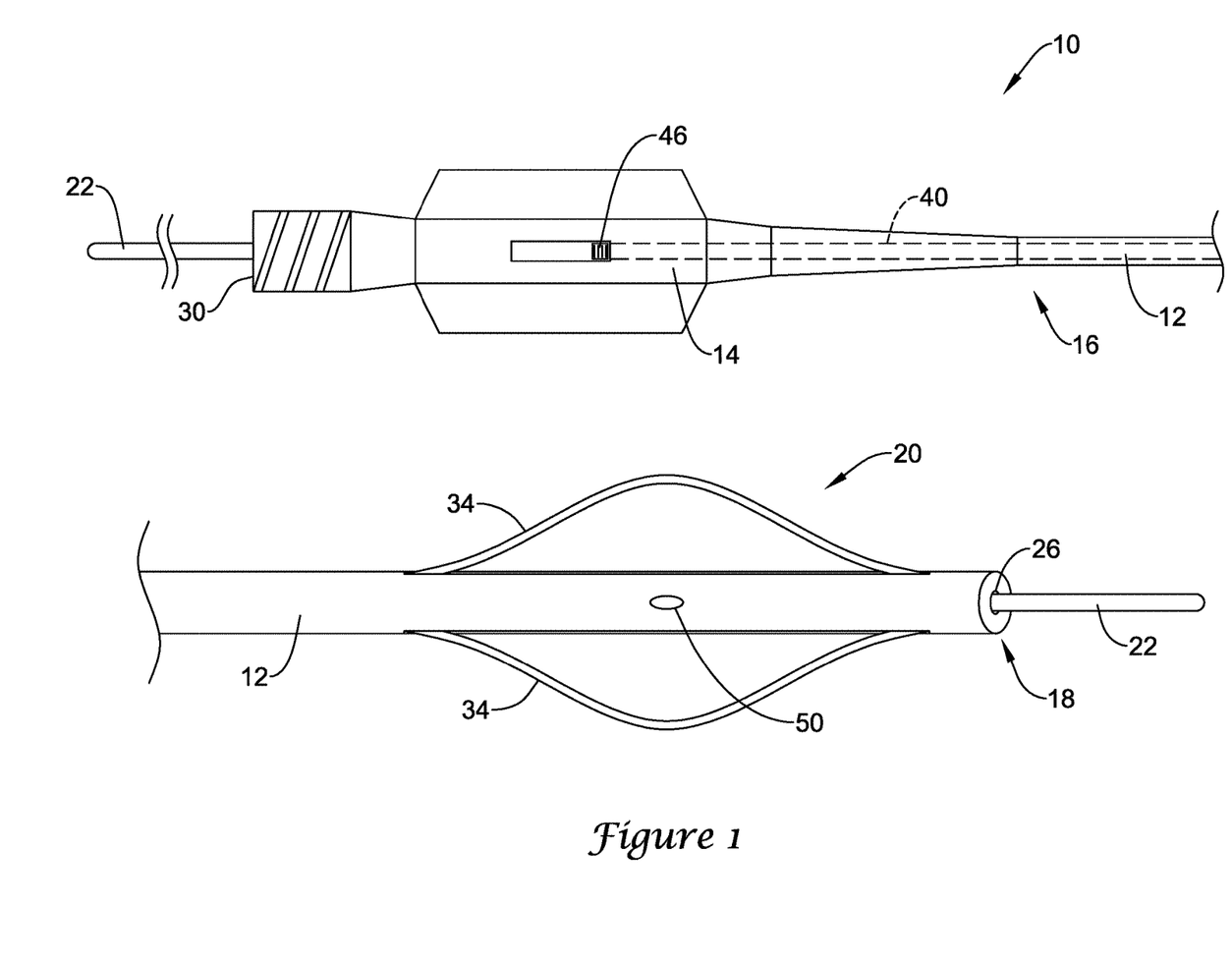
FIG. 1 is a plan view of an exemplary catheter apparatus for recanalization of a blood vessel.

An exemplary recanalization catheter 10 is illustrated at FIG. 1. The recanalization catheter 10 may include a catheter shaft 12 extending from a hub assembly 14 at a proximal end 16 of the catheter shaft 12 to an expandable member, shown as an expandable winged structure 20 mounted on a distal portion of the catheter shaft 12 proximate the distal end 18 of the catheter shaft 12. As will be described further herein, in some instances the expandable member may be formed of one or more, or a plurality of struts or wires which may be automatically or manually expanded, or other manually expandable or automatically expandable structure.

The catheter 10 may be configured to be advanced over a guidewire 22 for delivery to a remote location in the vasculature of a patient. For example, in some instances the catheter 10 may be configured as an over-the-wire (OTW) catheter having a guidewire lumen 24 (see FIG. 2) extending through the entire length of the catheter 10 from a distal port 26 at a distal tip of the catheter 10 to a proximal guidewire port 30 in the hub assembly 14. FIG. 1 illustrates such a configuration with a proximally extending portion of the guidewire 22 extending from the hub assembly 14 and a distally extending portion of the guidewire 22 extending from the distal port 26. In other instances, the catheter 10 may be configured as a single-operator-exchange (SOE) catheter having a guidewire lumen 24 extending from a distal port 26 to a proximal guidewire port (not shown) located a short distance proximal of the expandable winged structure 20 and distal of the hub assembly 14. In such a configuration, the guidewire 22 may extend through the guidewire lumen 24 between the distal port 26 and the proximal port, and extend along an exterior of the catheter shaft 12 proximal of the proximal port to the proximal end 16 of the catheter shaft 12. It is noted that in instances in which the catheter 10 is an SOE catheter, the hub assembly 14 may not include a proximal guidewire port 30.

Figure 2:
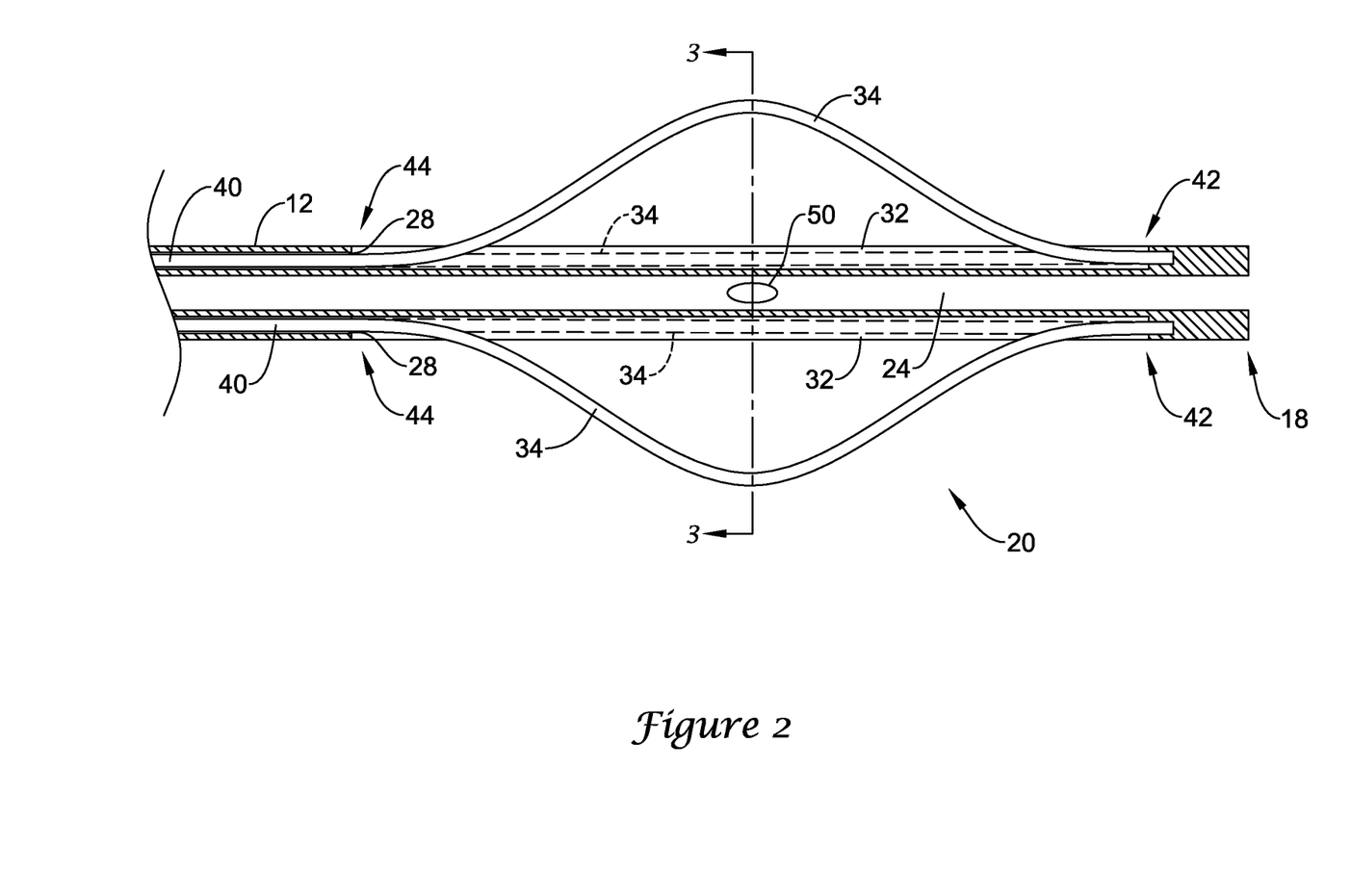
FIG. 2 is an exemplary cross-sectional view of the distal portion of the catheter of FIG. 1.

Turning to FIG. 2, the catheter shaft 12, or a portion thereof, may be an extruded shaft having one or more, or a plurality of lumens formed therein. For example, the catheter shaft 12 may include the guidewire lumen 24, and one or more, or a plurality of auxiliary lumens 28 extending therethrough. In some instances such as in the embodiment shown in FIG. 2, the guidewire lumen 24 may be positioned longitudinally between first and second auxiliary lumens 28. In other embodiments, the catheter shaft 12 may be formed of a plurality of tubular components defining one or more, or a plurality of lumens of the catheter shaft 12.

Figure 3:
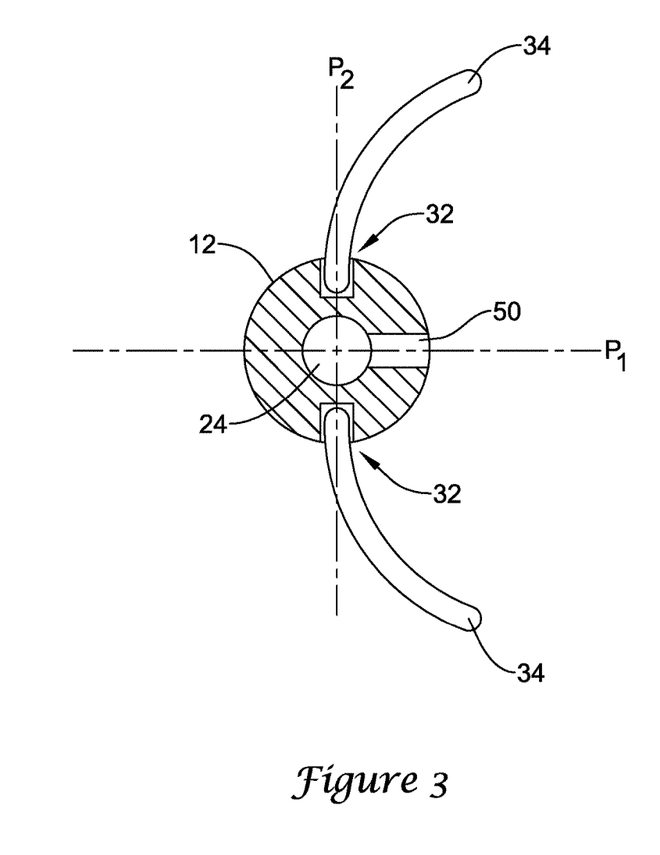
FIG. 3 is an exemplary cross-sectional view taken along line 3-3 of FIG. 2.

The guidewire lumen 24 may extend to the distal tip 18 of the catheter shaft 12, while the auxiliary lumens 28 may terminate proximal of the distal tip 18 of the catheter shaft 12. For example, each of the axillary lumens 28 may extend distally through the catheter shaft 12 to an elongate slot or channel 32 formed along a distal region of the catheter shaft 12. The elongate slot(s) or channel(s) 32 may open out to an exterior of the catheter shaft 12. For example, the catheter shaft 12 may include a pair of slots or channels 32 opening out on opposite sides of the catheter shaft 12. In some instances, as shown in FIG. 3, the first and second channels 32 may extend generally parallel to the longitudinal axis of the catheter shaft 12 and be positioned about 180° apart around the perimeter of the catheter shaft 12 with the guidewire lumen 24 positioned longitudinally between the first and second elongate channels 32.

In some instances the auxiliary lumens 28 may extend proximally from the elongate channels 32 to the hub assembly 14, or the auxiliary lumens 28 may converge to a single auxiliary lumen extending to the hub assembly 14. In other instances, the auxiliary lumens 28 may converge into the guidewire lumen 24 with the wires 40 extending through the guidewire lumen 24 to the hub assembly 14. For example, in some instances, the auxiliary lumens 28 may be passages extending into the guidewire lumen 24 from the proximal ends 44 of the channels 32.

The expandable winged structure 20 may include a first mechanically actuatable wing 34 extendable from the first channel 32 and a second mechanically actuatable wing 34 extendable from the second channel 32. The actuatable wings 34 may be actuatable between a retracted position and an expanded position. For example, in the retracted position (shown in dashed lines) the first and second mechanically actuatable wings 34 extend generally parallel to the longitudinal axis of the catheter shaft 12 and may be positioned in the first and second elongate channels 32, respectively. In the expanded position the first and second mechanically actuatable wings 34 may curve away from the longitudinal axis of the catheter shaft 12 and extend outward from the first and second elongate channels 32, respectively. For instance, the distal region of the elongate shaft 12 may have an outer periphery such that in the retracted position (shown in dashed lines) the first and second actuatable wings 34 may be positioned radially inward of the outer periphery of the elongate shaft 12 and in the expanded position the first and second actuatable wings 34 may be positioned radially outward of the outer periphery of the elongate shaft 12.

The catheter 10 may include an actuation mechanism configured to mechanically actuate the actuatable wings 34 between the retracted position and the expanded position. An exemplary actuation mechanism may include a first wire 40 extending through the first auxiliary lumen 28 of the catheter shaft 12 and/or a second wire extending through the second auxiliary lumen 28 of the catheter shaft 12. The first wire 40 may be configured to be actuated proximally and distally through the first auxiliary lumen 28 to actuate the first actuatable wing 34 between the retracted position and the expanded position. Similarly, the second wire 40 may be configured to be actuated proximally and distally through the second auxiliary lumen 28 to actuate the second actuatable wing 34 between the retracted position and the expanded position. In other instances both of the wires 40 may extend through a single auxiliary lumen 28 or through the guidewire lumen 24 to actuate the actuatable wings 34. It is noted that in some instances, a single wire 40, extending through an auxiliary lumen 28 or through the guidewire lumen 24, may be used to actuate both the first and second actuatable wings 34.

It is noted that in some embodiments the actuatable wings 34 may be automatically actuatable from the retracted position to the expanded position, such as through the proximal withdrawal of an outer sheath extending over the actuatable wings 34 in the retracted position. For example, an outer sheath could be provided surrounding the distal region of the catheter shaft 12 retaining the actuatable wings 34 in the elongate channels 32. Proximal movement of the outer sheath relative to the catheter shaft 12 may expose the actuatable wings 34 from the distal end of the outer sheath and thus no longer restrain the actuatable wings 34, permitting the actuatable wings 34 to revert to or toward a preset curved configuration.

As shown in FIG. 2, in some instances the first actuatable wing 34 may be formed as a distal portion of the first wire 40 and the second actuatable wing 34 may be formed as a distal portion of the second wire 40. However, in other embodiments, the first and second actuatable wings 34 may be formed as discrete members attached to the first and second wires 40, for example. The first and second actuatable wings 34 and the first and second wires 40 may be formed of any desired material, such as metallic or polymeric materials, and may have any desired cross-section, including circular, oval, rectangular, etc. In some instances, the actuatable wings 34 may be formed of a radiopaque material, or include radiopaque elements permitting visualization of the actuatable wings 34 in the anatomy during a medical procedure using fluoroscopy, for example.

As shown in FIG. 2, the distal end of the first actuatable wing 34 (e.g., the distal end of the first wire 40) may be affixed to the elongate shaft 12 proximate a distal end 42 of the first channel 32 and a distal end of the second actuatable wing 34 (e.g., the distal end of the second wire 40) may be affixed to the elongate shaft 12 proximate a distal end 42 of the second channel 32. Furthermore, a proximal end of the first actuatable wing 34 (e.g., a proximal portion of the first wire 40) may extend into the first auxiliary lumen 28 proximate the proximal end 44 of the first channel 32 and a proximal end of the second actuatable wing 34 (e.g., a proximal portion of the second wire 40) may extend into the second auxiliary lumen 28 proximate the proximal end 44 of the second channel 32.

As shown in FIG. 1, the wire(s) 40 may extend through the elongate shaft 12 to an actuator 46, such as a button, switch, lever, knob, etc., which may be positioned in the hub assembly 14, for example. The clinician may actuate the actuator 46 to effect expansion and/or retraction of the actuatable wings 34 at the distal region of the catheter shaft 12. For example, moving the actuator 46 distally may actuate the wire(s) 40 distally and in turn actuate the actuatable wings 34 to the expanded position. Likewise, moving the actuator 46 proximally may actuate the wire(s) 40 proximally and in turn actuate the actuatable wings 34 to the retracted position.

The distal region of the elongate shaft 12 may also include a lateral opening or port 50, as shown in FIGS. 1-3. The lateral port 50 may be in communication with the guidewire lumen 24, or another lumen extending through the elongate shaft 12. The lateral port 50 may be configured to permit a penetration member to be advanced therefrom during a recanalization procedure to puncture through a tissue layer of a vessel wall from the subintimal space into the true lumen of a blood vessel. For example, a distal portion of a penetration member, which may be advanced through the guidewire lumen 24, may pass laterally from the catheter shaft 12 out through the lateral port 50 to penetrate through a tissue layer of a blood vessel. In some instances, the lateral port 50 may be located in the distal region of the catheter shaft 12 at a location between the proximal ends 44 and the distal ends 42 of the channels 32. In other instances, the lateral port 50 may be otherwise located in the distal region of the catheter shaft 12, such as proximal of the proximal end 44 of the elongate channels 32 or distal of the distal end 42 of the elongate channels 32.

In some instances, the lateral port 50 may be located equidistantly between the first and second elongate channels 32. For example, as shown in FIG. 3, the lateral port 50 may be arranged on the perimeter of the catheter shaft 12 an equal distance around the perimeter from each of the elongate channels 32. In other words, the lateral port 50 may be centrally positioned on the perimeter of the catheter shaft 12 between the elongate channels 32 in some instances. For example, as shown in the embodiment of FIG. 3, the lateral port 50 may be positioned about 90° from each of the elongate channels 32 around the perimeter of the catheter shaft 12.

The first and second actuatable wings 34 may be configured to curve from the elongate channels 32 towards the lateral port 50 in the expanded position such that the lateral port 50 is oriented toward a true lumen of a blood vessel when the first and second actuatable wings 34 are in the expanded position in the subintimal space formed in the vessel wall. For example, as shown in FIG. 3, when viewed along the longitudinal axis of the catheter shaft 12, the actuatable wings 34 may extend in an arcuate path away from the elongate shaft 12 in the expanded position to be positionable in a circumferential orientation within a subintimal space formed in a vessel wall. In other words, the outermost extents of the actuatable wings 34 (i.e., the portion of the actuatable wings 34 furthest from the catheter shaft 12) in the expanded position may be curved toward a plane $P_1$ passing through the lateral port 50 and extending parallel to the central longitudinal axis of the catheter shaft 12 while curving away from a plane $P_2$ extending parallel to the central longitudinal axis of the catheter shaft 12 and perpendicular to the plane $P_1$. The outermost extents of the actuatable wings 34 may curve away from the plane $P_2$ on a common side of the plane $P_2$ which may be the same side of the plane $P_2$ having the lateral port 50. Thus, in the expanded position, the outermost extents of the actuatable wings 34 may be positioned further from the plane $P_2$ than portions of the actuatable wings 34 proximate the proximal ends 44 and distal ends 42 of the elongate channels 32.

In some embodiments, the first and second actuatable wings 34 may have a preset circumferential curvature, such as shown in FIG. 3, such that the first and second actuatable wings 34 automatically curve from the elongate shaft 12 when actuated to the expanded position. For example, the first and second actuatable wings 34 may be formed of a shape memory material (e.g., shape memory polymer or shape memory metal, such as nitinol) such that the first and second actuatable wings 34 automatically return to their preset or memorized curved shape when actuated from the retracted position to the expanded position.

Figure 4:
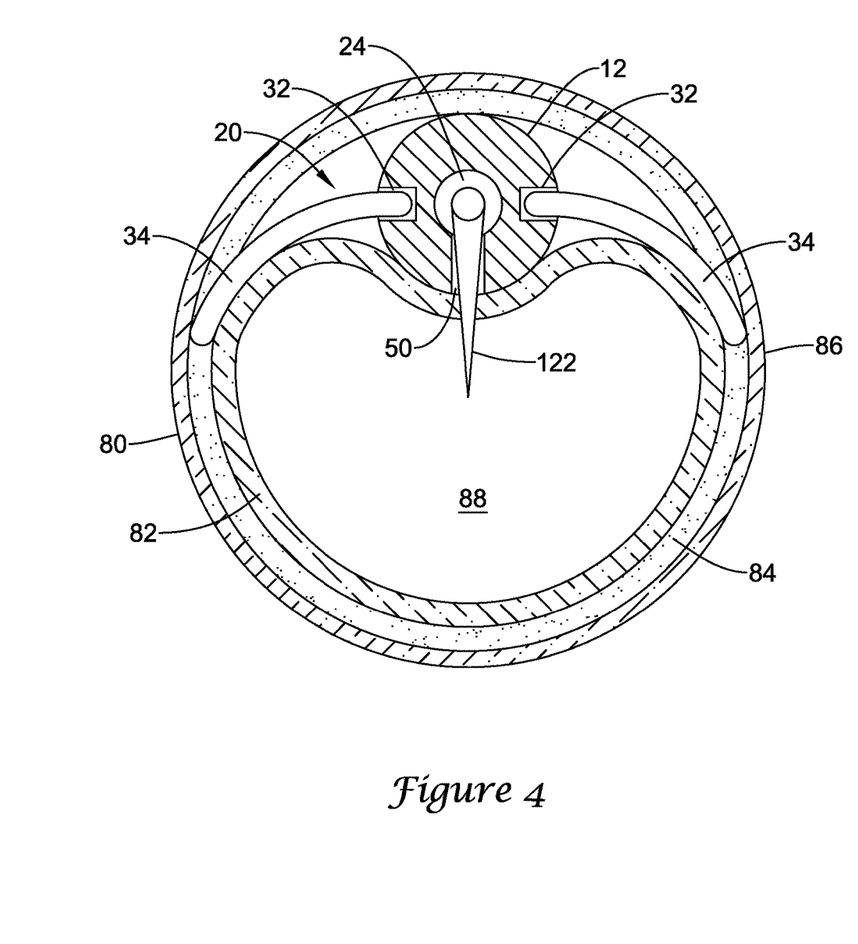
FIG. 4 is a cross-sectional view of the catheter apparatus positioned in the subintimal space of a blood vessel.

FIG. 4 is a cross-sectional view of the distal region of the catheter shaft 12 positioned in a subintimal space created between two tissue layers of a vessel wall 80. The blood vessel 80 typically has three tissue layers, an innermost layer or intima layer (i.e., tunica intima) 82, an intermediate layer or media layer (i.e., tunica media) 84, and an outermost layer or adventitia layer (tunica adventitia) 86, with the media layer 84 positioned between the intima layer 82 and the adventitia layer 86. The intima layer 82 is a layer of endothelial cells lining the lumen 88 of the vessel 80, as well as a subendothelial layer made up of mostly loose connective tissue. The media layer 84 is a muscular layer formed primarily of circumferentially arranged smooth muscle cells. The adventitia layer 86, which forms the exterior layer of the vessel wall 80 is formed primarily of loose connective tissue made up of fibroblasts and associated collagen fibers.

As will be described further herein, the distal portion of the catheter shaft 12, including the expandable winged structure 20, may be advanced into a subintimal space (i.e., a space between the intima layer 82 and the adventitia layer 86) created in the vessel wall 80, such as through dissection of the tissue layers of the vessel wall 80. Once positioned in the subintimal space, the actuatable wings 34 of the expandable winged structure 20 may be actuated to the expanded position between the intima layer 82 and the adventitia layer 86 of the vessel wall 80. As the actuatable wings 34 are actuated to the expanded position, the wings 34 extend in an arcuate path away from the elongate shaft 12 in a circumferential orientation within the subintimal space formed in the vessel wall 80 to automatically orient the lateral port 50 radially inward toward the true lumen 88 of the blood vessel. Thus, the curvature of the actuatable wings 34 in the expanded state may conform to or approximate the curvature of the vessel wall 80 around the circumference of the vessel wall 80.

The extent to which the actuatable wings 34 are expanded may be controlled by the amount of distal movement of the wire(s) 40 through the catheter shaft 12. In other words, greater distal actuation of the wire(s) 40 relative to the catheter shaft 12 may result in greater expansion of the actuatable wings 34. For example, the actuation wire(s) 40 may be actuated distally a first amount to effect expansion of the actuatable wings 34 a first amount, whereas the actuation wire(s) 40 may be actuated distally a second amount (greater than the first amount of distal actuation) to effect expansion of the actuatable wings 34 a second amount (greater than the first amount of expansion). Thus, the extent the actuatable wings 34 are expanded may be tailored to the size of the blood vessel being treated (i.e., actuated to a smaller wing size for smaller blood vessels or actuated to a larger wing size for larger blood vessels).

A penetration member 122 may be advanced through the guidewire lumen 24, or other device delivery lumen, and out through the lateral port 50 to penetrate through the intima layer 82 into the true lumen 88 from the subintimal location. In some instances, the penetration member 122 may include a sharpened tip or stylet to facilitate penetration of the intima layer 82. In some instances, the penetration member 122 may include a curved distal tip permitting the penetration member 122 to advance out through the lateral port 50 when the distal tip encounters the lateral port 50. In other instances, the recanalization catheter 10 may include a deflection mechanism to deflect the penetration member 122 out through the lateral port 50.

Figure 5:
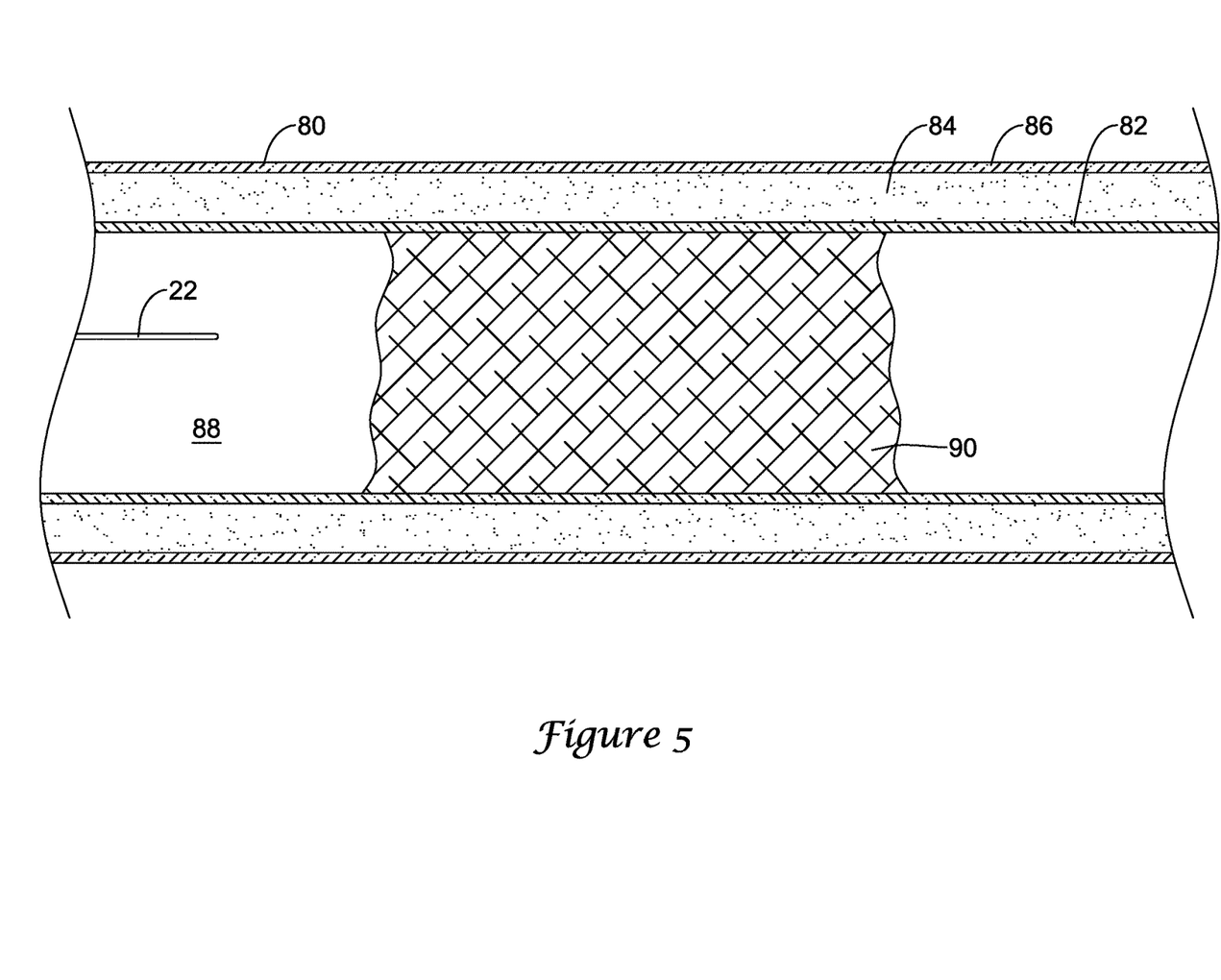
FIGS. 5-9 illustrate aspects of an exemplary method for recanalizing an occluded blood vessel using the catheter apparatus of FIG. 1.
Figure 6:
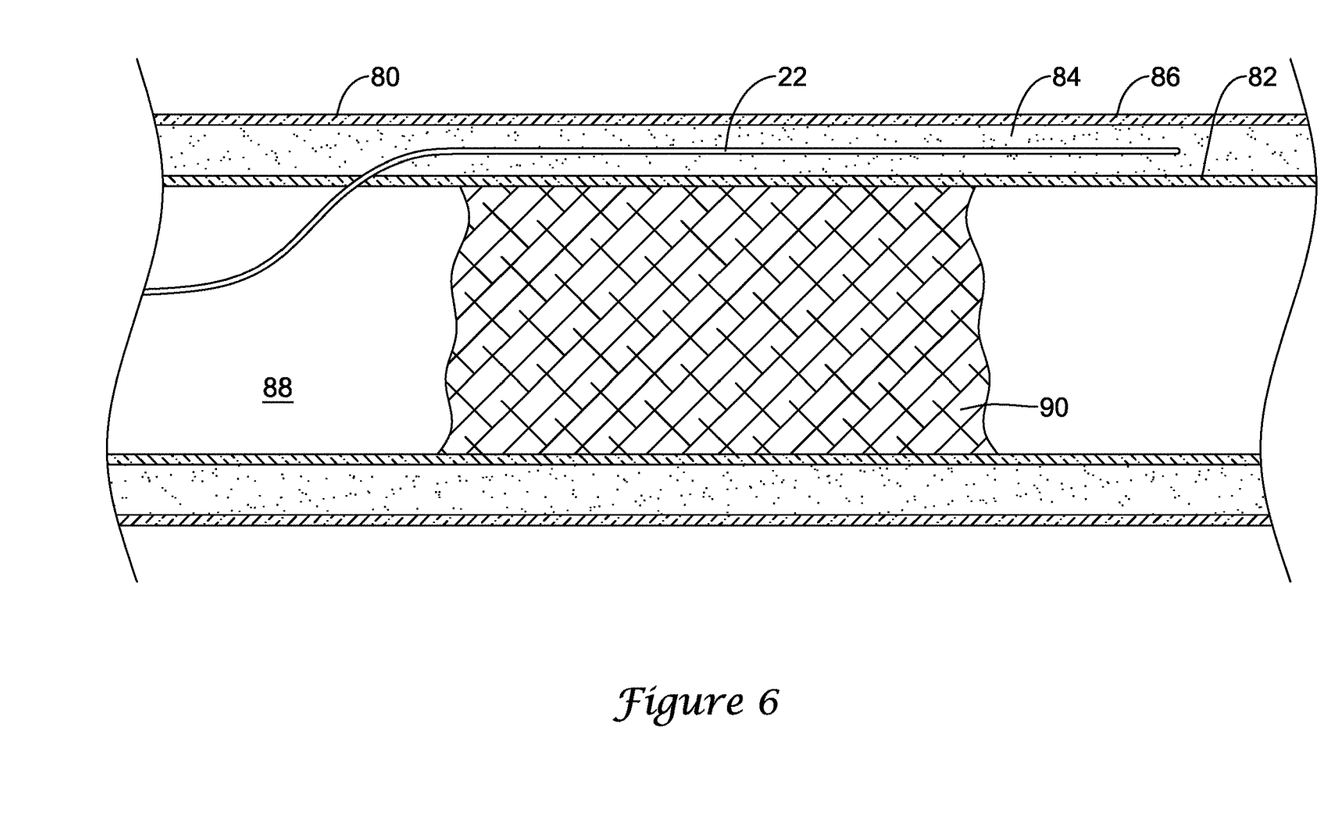

In some instances, it may be undesired, difficult or impossible to pass through an occlusion, such as a chronic total occlusion (CTO) in a lumen of a blood vessel with a medical device to recanalize the vessel. In such instances, it may be possible to recanalize the blood vessel through a subintimal approach using the catheter 10. Turning to FIGS. 5-9, several aspects of an exemplary method for recanalizing an occluded blood vessel using the catheter 10 are illustrated. As shown in FIG. 5, a guidewire 22 may initially be advanced through the lumen 88 of the vessel 80 to a location proximate a proximal end of an occlusion 90 blocking the lumen 88. The guidewire 22 may then be advanced to penetrate outward through the intima layer 82 at a location proximal of the proximal end of the occlusion 90 into the vessel wall 80. With the tip of the guidewire 22 located between the intima layer 82 and the adventitia layer 86, the guidewire 22 may be further advanced distally in a subintimal manner to create a subintimal space between the intima layer 82 and the adventitia layer 86. As shown in FIG. 6, the guidewire 22 may be advanced in a subintimal manner until the distal tip of the guidewire 22 is located distal of the distal end of the occlusion 90 in the subintimal space created, such as by dissection of the tissue layers of the vessel wall 80. In some instances another catheter device may be initially used to exit the lumen 88 proximal of the occlusion 90 and form a subintimal space. In such an instance, the guidewire 22 may be subsequently advanced through the catheter into the subintimal space and the catheter may be withdrawn, leaving the guidewire positioned in the subintimal space as shown in FIG. 6.

Figure 7:
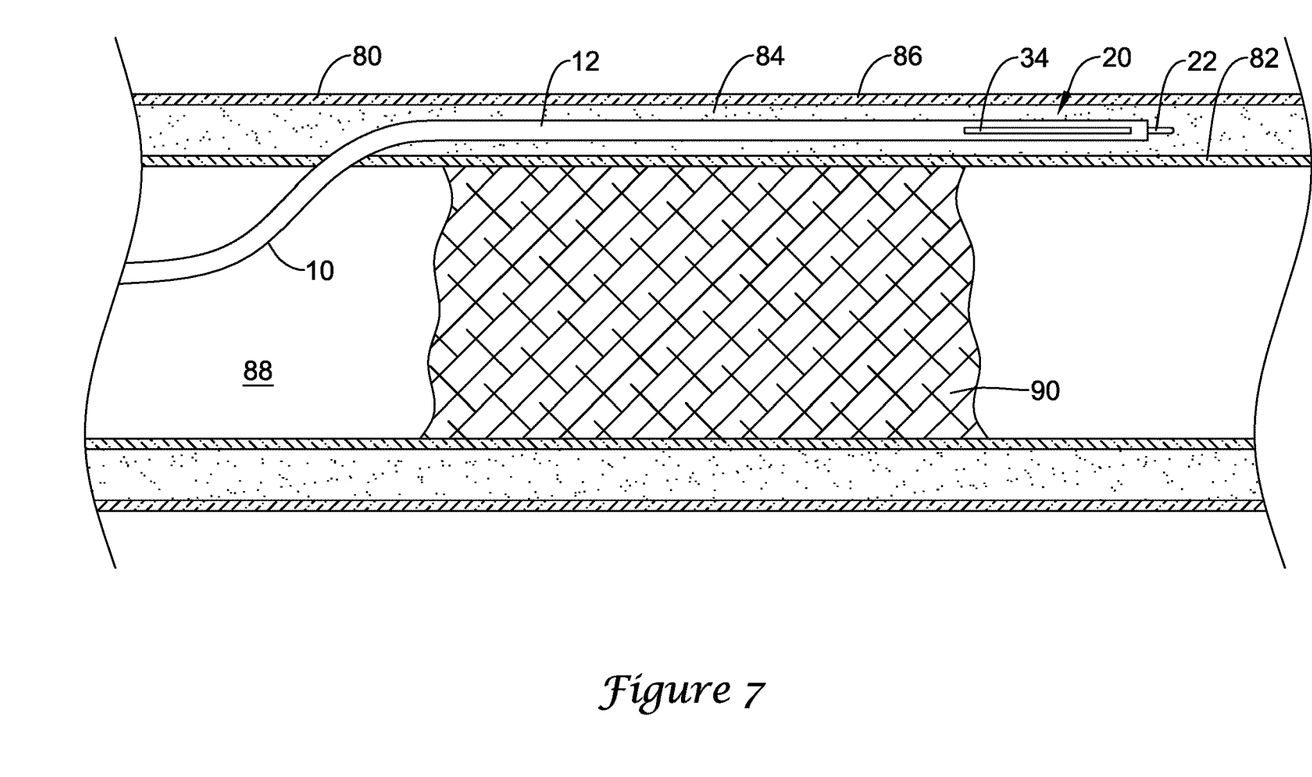

The recanalization catheter 10 may then be advanced distally over the guidewire 22 from the true lumen 88 proximal of the occlusion 90, into the subintimal space between the intima layer 82 and the adventitia layer 86, to a position in the subintimal space in which the distal portion of the catheter 10, including the expandable winged structure 20, is located distal of the distal end of the occlusion 90, as shown in FIG. 7. The recanalization catheter 10 may be advanced through the subintimal space in a delivery configuration, such as with the actuatable wings 34 in the retracted position such that the actuatable wings 34 do not increase the profile of catheter shaft 12 during delivery of the expandable winged structure 20 to the subintimal space. In some instances in which the catheter 10 is configured with a distal tip to facilitate piercing and/or dissection of tissue layers of the blood vessel, a sharp, rigid or piercing feature of the distal tip may be used to pierce and/or dissect tissue layers of the vessel wall 80 as the catheter 10 is advanced distally.

Figure 8:
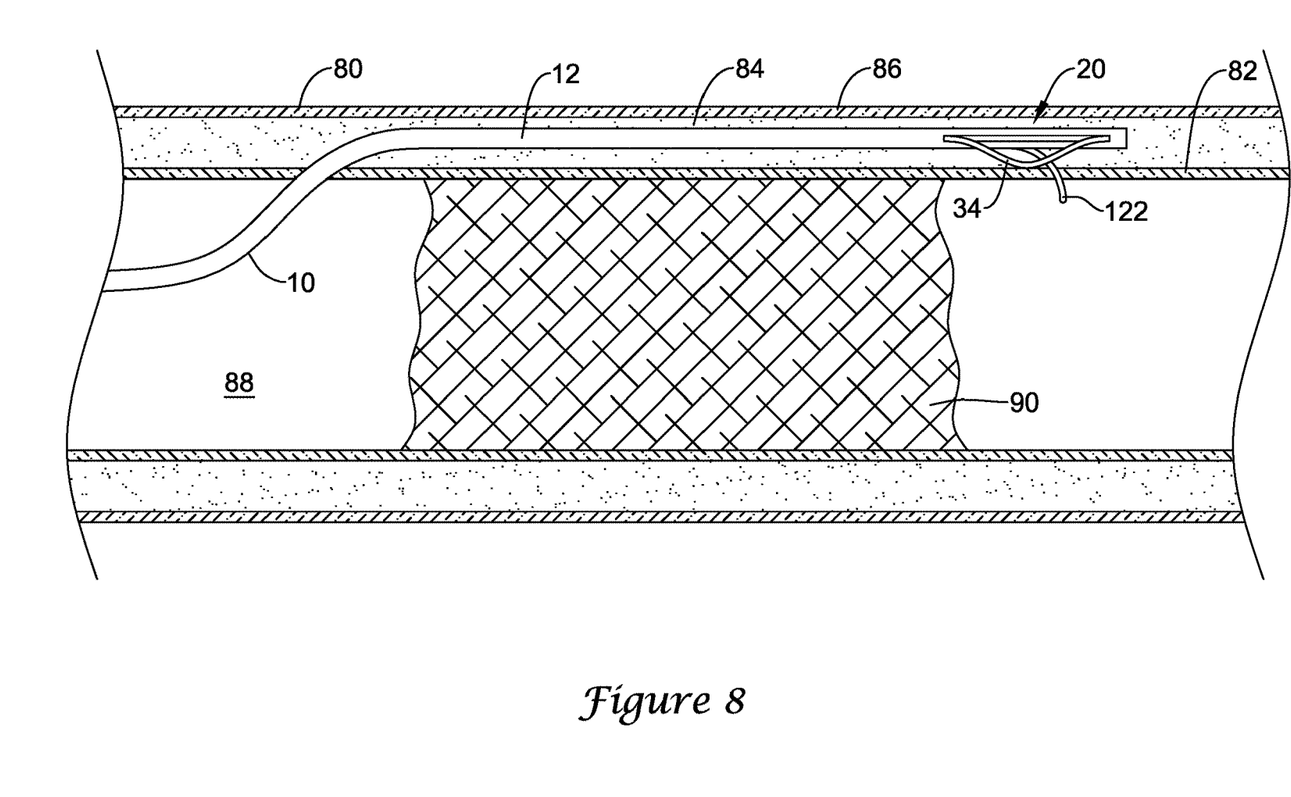

With the lateral port 50 and expandable winged structure 20 positioned distal of the distal end of the occlusion 90, the actuatable wings 34 may be expanded in the subintimal space formed between the intima layer 82 and the adventitia layer 86, as shown in FIG. 8. As the actuatable wings 34 are actuated to the expanded position, the wings 34 may extend in an arcuate path away from the catheter shaft 12 in a circumferential orientation within the subintimal space formed in the vessel wall 80 to automatically orient the lateral port 50 radially inward toward the true lumen 88 of the blood vessel, as shown in FIG. 4.

The guidewire 22 may be withdrawn from the guidewire lumen 24, and an elongate penetration member 122 may then be advanced through the guidewire lumen 24 of the catheter 10 and exit the lateral port 50 to penetrate through the intima layer 82 into the true lumen 88 distal of the occlusion 90, shown in FIG. 8. In some embodiments, the penetration member 122 may be the guidewire 22, or another guidewire introduced through the guidewire lumen 24 of the catheter shaft 12. In other embodiments, the penetration member 122 may be an elongate member, such as a needle cannula or stylet, having a sharpened distal tip configured to pierce through the intima layer 82 into the lumen 88 distal of the occlusion 90.

Figure 9:
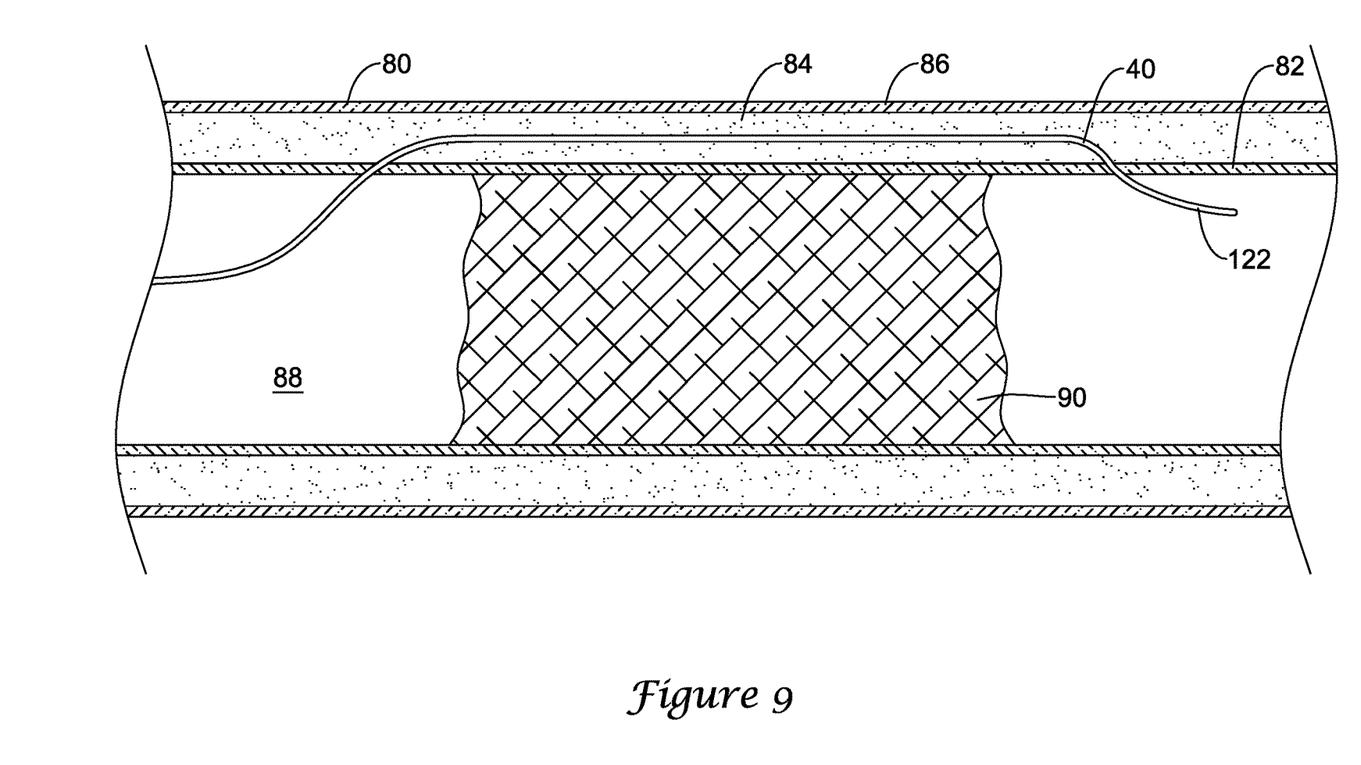

In the event the penetration member 122 is a guidewire, the catheter 10 may be withdrawn while leaving the guidewire routed around the occlusion 90 via the subintimal pathway, such as shown in FIG. 9. In instances in which the penetration member 122 is a separate elongate member, such as a needle cannula or stylet, the penetration member 122 may be withdrawn and replaced with a guidewire. The catheter 10 and/or penetration member 122 may be withdrawn while leaving the guidewire routed around the occlusion 90 via the subintimal pathway.

Once a pathway has been created across the occlusion 90, (e.g., around the occlusion 90 via a subintimal track), one or more additional medical devices may be advanced through the blood vessel 80 to enlarge the pathway and/or pass distally of the occlusion 90 to perform a further medical procedure.

Those skilled in the art will recognize that aspects of the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A recanalization catheter for facilitating re-entry into a lumen of a blood vessel from a subintimal space, comprising:
   an elongate shaft extending distally from a hub assembly, the elongate shaft including a guidewire lumen extending along a longitudinal axis of the elongate shaft;
   first and second actuatable wings positioned at a distal region of the elongate shaft, the first and second actuatable wings being actuatable between a retracted position and an expanded position;
   the elongate shaft including a lateral port positioned between the first and second actuatable wings;
   wherein in the expanded position the first and second actuatable wings extend radially outward on opposite sides of the elongate shaft along an arcuate path;
   wherein in the expanded position, an outermost extent of the first actuatable wing curves toward a first plane extending through and parallel to the longitudinal axis which passes through the lateral port and away from a second plane extending perpendicular to the first plane;
   wherein in the expanded position, an outermost extent of the second actuatable wing curves toward the first plane and away from the second plane; and
   wherein the first actuatable wing extends outward from a first channel in the elongate shaft and the second actuatable wing extends outward from a second channel in the elongate shaft.

2. The recanalization catheter of claim 1, wherein the distal region of the elongate shaft has an outer periphery, wherein in the retracted position the first and second actuatable wings are positioned radially inward of the outer periphery of the elongate shaft and in the expanded position the first and second actuatable wings are positioned radially outward of the outer periphery of the elongate shaft.

3. The recanalization catheter of claim 1, wherein the first and second actuatable wings are configured to orient the lateral port toward the lumen of the blood vessel when the first and second actuatable wings are in the expanded position in the subintimal space.

4. The recanalization catheter of claim 1, wherein the lateral port is in communication with the guidewire lumen.

5. The recanalization catheter of claim 1, further comprising an actuator on the hub assembly configured to actuate the first and second actuatable wings from the retracted position to the expanded position.

6. The recanalization catheter of claim 1, wherein the lateral port is located between proximal and distal extents of the first and second actuatable wings.

7. The recanalization catheter of claim 1, wherein a distal end of the first actuatable wing is secured to the elongate shaft, and a distal end of the second actuatable wing is secured to the elongate shaft.

8. The recanalization catheter of claim 1, wherein the first and second actuatable wings have a preset circumferential curvature such that the first and second actuatable wings automatically curve from the elongate shaft when actuated to the expanded position.

9. The recanalization catheter of claim 1, further comprising a re-entry device extendable from the lateral port into the lumen of the blood vessel.

10. The recanalization catheter of claim 1, wherein the first actuatable wing is formed of a distal portion of a first wire extending through the elongate shaft and the second actuatable wing is formed of a distal portion of a second wire extending through the elongate shaft.

11. The recanalization catheter of claim 10, wherein the first and second wires extend to an actuator on the hub assembly.

12. A recanalization catheter for facilitating re-entry into a lumen of a blood vessel from a subintimal space, comprising:
   an elongate shaft extending distally from a hub assembly, the elongate shaft including a guidewire lumen extending along a longitudinal axis of the elongate shaft and a lateral port extending through a wall of the elongate shaft to the guidewire lumen;
   first and second actuatable wings positioned on opposite sides of the elongate shaft with distal ends of each of the first and second actuatable wings secured to the elongate shaft, the first and second actuatable wings being actuatable between a retracted position and an expanded position;
   wherein in the expanded position the first and second actuatable wings extend radially outward on opposite sides of the elongate shaft along a circumferentially arcuate path;
   wherein in the expanded position, an outermost extent of the first actuatable wing circumferentially curves toward a first plane extending through and parallel to the longitudinal axis which passes through the lateral port and away from a second plane extending perpendicular to the first plane;

wherein in the expanded position, an outermost extent of the second actuatable wing circumferentially curves toward the first plane and away from the second plane; and wherein the first actuatable wing extends outward from a first channel in the elongate shaft and the second actuatable wing extends outward from a second channel in the elongate shaft.

13. The recanalization catheter of claim 12, wherein the first actuatable wing is formed of a distal portion of a first wire extending through the elongate shaft and the second actuatable wing is formed of a distal portion of a second wire extending through the elongate shaft.

14. The recanalization catheter of claim 13, wherein the first and second wires extend to an actuator on the hub assembly.

15. The recanalization catheter of claim 13, wherein the first wire extends through a first auxiliary lumen extending through the elongate shaft and the second wire extends through a second auxiliary lumen extending through the elongate shaft.

16. The recanalization catheter of claim 15, wherein the first and second wires extend to an actuator on the hub assembly.

17. The recanalization catheter of claim 15, wherein the guidewire lumen is positioned longitudinally between the first and second auxiliary lumens.

18. The recanalization catheter of claim 12, wherein the first and second actuatable wings are configured to orient the lateral port toward the lumen of the blood vessel when the first and second actuatable wings are in the expanded position in the subintimal space.

* * * * *